(12) United States Patent
LeMay (10) Patent No.: US 9,291,654 B2
(45) Date of Patent: Mar. 22, 2016

(54) PATIENT ELECTRODE IMPEDANCE MEASUREMENT

(75) Inventor: Charles LeMay, Portsmouth, NH (US)

(73) Assignee: Draeger Medical Systems, Inc., Andover, MA (US)

( * ) Notice: Subject to any disclaimer, the term of this patent is extended or adjusted under 35 U.S.C. 154(b) by 0 days.

(21) Appl. No.: 14/358,306

(22) PCT Filed: Nov. 18, 2011

(86) PCT No.: PCT/US2011/061354
§ 371 (c)(1),
(2), (4) Date: May 15, 2014

(87) PCT Pub. No.: WO2013/074114
PCT Pub. Date: May 23, 2013

(65) Prior Publication Data
US 2014/0257119 A1    Sep. 11, 2014

(51) Int. Cl.
*A61B 5/04*    (2006.01)
*G01R 27/02*    (2006.01)
*A61B 5/00*    (2006.01)
*A61B 5/0428*    (2006.01)
*A61B 5/0402*    (2006.01)
*A61B 5/053*    (2006.01)

(52) U.S. Cl.
CPC .............. *G01R 27/02* (2013.01); *A61B 5/0402* (2013.01); *A61B 5/04288* (2013.01); *A61B 5/6844* (2013.01); *A61B 5/7221* (2013.01); *A61B 5/053* (2013.01); *A61B 2560/0276* (2013.01)

(58) Field of Classification Search
CPC ... A61N 1/08; A61N 2001/083; A61B 5/0402
See application file for complete search history.

(56) References Cited

U.S. PATENT DOCUMENTS

| 4,417,590 A | 11/1983 | Smith et al. |
| 4,577,639 A | 3/1986 | Simon et al. |
| 2003/0163170 A1 | 8/2003 | Faisandier |

*Primary Examiner* — Joseph Dietrich
(74) *Attorney, Agent, or Firm* — Jones Day (57) ABSTRACT

An apparatus and method is provided that determines a connection quality of an electrode to a patient. A current source is connected to a first electrode and a switch is connected to a second electrode for selectively connecting the second electrode to ground. A processor is connected to the first electrode and a third electrode and the processor detects a voltage difference between the first electrode and the third electrode upon application of a current to the first electrode by the current source to determine connection quality data for the first electrode.

17 Claims, 7 Drawing Sheets

PATIENT ELECTRODE IMPEDANCE MEASUREMENT

The present application is a 35 USC §371 national stage application of International Application No. PCT/US2011/061354, filed Nov. 18, 2011, the entirety of which is incorporated herein by reference.

FIELD OF THE INVENTION

This invention concerns a system and method for patient monitoring devices and, more specifically, for measuring the impedance of an electrode from a set of electrodes connected to a patient to determine a connection quality associated with the electrode.

BACKGROUND OF THE INVENTION

In the course of providing healthcare to patients, it is necessary to monitor vital statistics and other patient parameters. A plurality of different patient monitoring devices are able to selectively monitor the electrical impulses generated by a patient via at least one electrode that is coupled to the skin of the patient at particular locations on the body of the patient. One type of patient monitoring device is an electrocardiogram (ECG) monitor. The ECG monitor is connected to the patient by a plurality of electrodes that monitor the electrical impulses of the patient's heart. In order for the ECG monitor to effectively monitor the electrical impulses of the patient, the electrodes conventionally include a conductive gel that is embedded in an adhesive pad. Wires from the monitor are selectively connected to the electrode in order to communicate voltages detected thereby to the ECG monitoring device to provide a healthcare practitioner with data regarding the patients heart function. A problem exists when the conducting gel degrades or the electrode otherwise dislodges itself from the patient. This results in noise in the signal being monitored. The connection quality for each lead is conventionally measured by cycling through each lead and identifying a resistance associated with the lead. However, a drawback associated with this is that this measurement is performed prior to monitoring the patient. It is therefore desirable to determine the connection quality for each electrode connected to a patient during the course of monitoring the patient. A system according to invention principles addresses deficiencies of known systems.

SUMMARY OF THE INVENTION

In one embodiment, an apparatus is provided that determines a connection quality of an electrode to a patient. A current source is connected to a first electrode and a switch is connected to a second electrode for selectively connecting the second electrode to ground. A processor is connected to the first electrode and a third electrode and the processor detects a voltage difference between the first electrode and the third electrode upon application of a current to the first electrode by the current source to determine connection quality data for the first electrode.

In another embodiment a method of determining a connection quality of an electrode connected to a patient is provided. The method includes connecting a first electrode of a plurality of electrodes to a processor, connecting a second electrode of a plurality of electrodes to ground and connecting a third electrode of a plurality of electrodes to the processor. A current is applied from a current source to the first electrode and a voltage difference between the first electrode and a third electrode is detected. Connection quality data of the first electrode is determined using the voltage difference between the first and third electrode.

In a further embodiment, an ECG monitoring apparatus that that determines a connection quality of an electrode connected to a patient is provided. A plurality of electrodes are coupled to a patient, each of said plurality of electrodes senses electrical impulses representing at least one patient parameter from the patient. A current source selectively connects the plurality of electrodes and selectively applies a current to any of the plurality of electrodes. A processor receives electrical impulses from the patient via the plurality of electrodes and calculates connection quality data for respective ones of the plurality of electrodes. A plurality of switches is provided, each switch is connected to a respective one of the plurality of electrodes and the processor and movable between a first position connecting a respective electrode to the processor and a second position connecting the respective electrode to ground. A first switch connects an electrode being monitored to the processor, and a second switch connects a second electrode to the processor. At least one other of the plurality of switches connects respective ones of the plurality of electrodes to ground. The processor detects a voltage difference between the first electrode and the second electrode upon application of a current to the first electrode by the current source to determine connection quality data for the first electrode.

DETAILED DESCRIPTION

The patient electrode impedance measurement apparatus (hereinafter "apparatus") automatically measures and calculates the impedance at the interface between the electrode and the patient. During the course of monitoring the electrical impulses of the patient, the apparatus advantageously provides a user (e.g. healthcare practitioner, doctor, nurse, etc.) with a measurement of the connection quality of the electrode to the patient. Connection quality data for a particular electrode is automatically determined using three electrodes that are connected to the patient being monitored. The connection quality data of an electrode is calculated by obtaining a voltage difference between a first electrode having a current applied thereto and a second electrode each connected to an amplifier. The third electrode in the arrangement is connected to ground such that the current (DC current) applied to the first electrode flows through the first electrode, through the patient and through the third electrode to ground. The amplifier determines the voltage difference between the first electrode and the second electrode and calculates an impedance by dividing the voltage difference between the first and second electrodes by the current applied to the first electrode. The resulting impedance is automatically compared to threshold impedance values to determine a connection quality whereby a lower impedance correlates to a stronger connection at the electrode/patient interface. The apparatus further advantageously enables a user to determine the connection quality of particular electrodes in order to identify which lead may be used as the drive lead. Typically, the drive lead is the lead with the strongest connection and identifying connection quality data for all leads advantageously provides healthcare practitioners with the flexibility to change the drive lead. The apparatus provides a further advantage by identifying the connection quality of electrodes to select a lead combination that provides highest quality ECG data. Moreover, the connection quality data provided by the apparatus enables a user to determine what combination of ECG leads may be used at a given time. Connection quality data may be acquired at startup and initial application of the electrodes to the patient as well as during the monitoring process.

Figure 1:
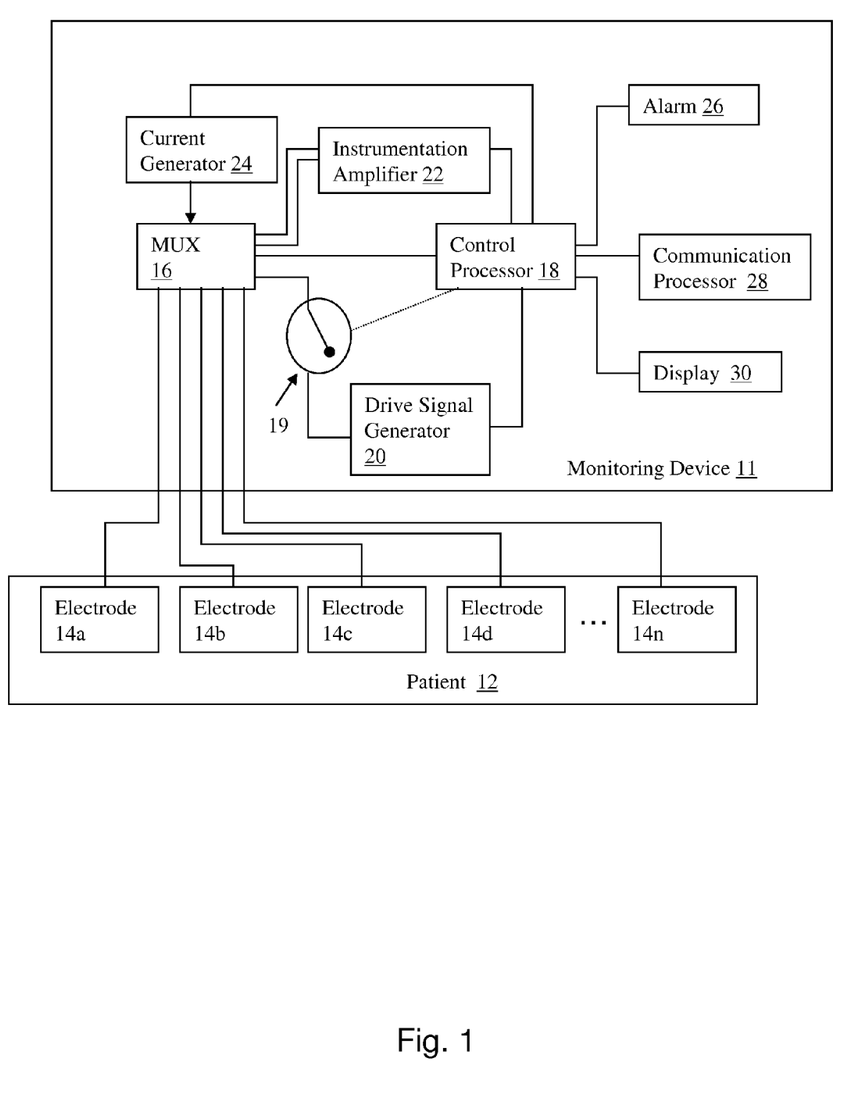
FIG. 1 is an exemplary block diagram of the patient electrode impedance measurement apparatus according to invention principles.

FIG. 1 is a block diagram of an exemplary patient monitoring device 11 that selectively monitors electrical impulses from a patient via a plurality of electrodes 14a-n that are connected to predetermined locations on the patient using a conductive gel and an adhesive. While electrodes 14a-n are shown herein, it should be appreciated that any number of electrodes may be used to monitor the electrical impulses of the patient and the number of electrodes 14n employed depends on the type of data being monitored by the monitoring device 11. In one embodiment, the patient monitoring device is an ECG monitor and the plurality of electrodes may include limb leads and chest leads. One skilled in the art understands that the limb leads include electrodes positioned on the right arm (RA), left arm (LA), right leg (RL) and left leg (LL). Of these electrodes, RA, LA and LL are generally designated primary leads and RL is generally the drive lead that provides the patient drive signal derived from any of the primary leads (or combination of primary leads). Additionally, the chest leads are known to include electrodes $V_1$-$V_6$ positioned at predetermined locations on the chest of the patient in a known manner. The manner in which the monitoring device monitors the electrical impulses to generate and output ECG waveforms is known and is not germane to the present invention and will not be discussed further.

The monitoring device 11 includes a control processor 18 that includes control logic to control the operation of the monitoring device 11. The control logic includes algorithms for monitoring the electrical impulses of a patient to produce patient parameter data (e.g. ECG waveform). The control processor 18 is connected to a multiplexer 16 which enables bidirectional communication between the electrodes 14a-14n on the patient and the monitoring device 11. A drive signal generator 20 is connected between the control processor 18. The drive signal generator 20 generates and provides a drive signal (reference voltage) to an electrode designated as the drive lead and is connected to the multiplexer 16 via switch 19. For purposes of example, electrode 14d may be considered the drive lead. However, one skilled in the art will recognize that any electrode may be designated as the drive lead. The switch 19 is responsive to a control signal generated by the control processor 18 and is moveable between a first open position disconnecting the drive signal generator 20 from the multiplexer 16 and placing the drive signal generator in an inactive state whereby no patient drive signal is provided and a second closed position which completes a circuit between the control processor 18 and multiplexer 16 via the drive signal generator 20 placing the drive signal generator 20 in an active state and providing a patient drive signal via the patient drive electrode 14d. In another embodiment, the switch 19 is either absent or positioned within the drive signal generator 20 such that the control processor 18 may selectively provide a drive control signal to the drive signal generator 20 that controls whether or not the drive signal generator 20 is inactive (no patient drive signal is provided to the multiplexer 16) or active (patient drive signal is provided to the multiplexer 16).

An instrumentation amplifier 22 is connected between the control processor 18 and the multiplexer 16 and compares a voltage difference between two electrodes connected to the patient 12. The instrumentation amplifier 22 provides voltage differential data to the control processor 18 for use in calculating an impedance on a respective one of the plurality of electrodes 14a-14n connected to the patient. A current generator 24 is also connected between the control processor 18 and the multiplexer 16. The control processor 18 causes the current generator to apply a predetermined current to a selected one of the electrodes 14a-14n to determine the impedance of the selected electrode.

In operation, the control processor 18 selectively determines connection quality data for each electrode 14a-14n connected to the monitoring device 11. The connection quality data may be determined at start up and initial connection of the electrodes 14a-14n to the patient or during monitoring of the patient. In either instance, the control processor 18 causes the switch 19 to move into the open position disconnecting the drive signal generator 20 from the multiplexer 16 and preventing a patient drive signal to be provided on the patient drive lead. The control processor 18 identifies and selects a first electrode 14a from the set of electrodes to determine the quality of the connection to the patient and identifies and selects a second electrode 14b as a comparison electrode. The control processor 18 further configures a third electrode 14c to be connected to ground. The configuration of the electrodes as discussed above is performed by switches in the multiplexer in a known manner. Upon identifying and selecting the electrode on which the connection quality data measurement is to be performed, the current generator 24 is configured to apply a current to the selected electrode 14a. Current flows through the first electrode 14a, through the patient and through the third electrode 14c to ground. As the current flows through the patient, a voltage on the first selected electrode 14a and the second comparison electrode 14b is sensed. The control processor 18 automatically calculates a voltage difference between the selected electrode 14a and the comparison electrode 14b and the impedance of the selected electrode is calculated by dividing the voltage difference by the current applied to the selected electrode. The resulting electrode impedance is compared to a threshold impedance to produce connection quality data for the selected electrode. If the resulting electrode impedance is below the threshold level, the connection quality is good whereas if the resulting impedance is equal to or greater than the threshold level, the connection quality is poor. For example, electrode impedance may range between 50 kns and several mega ohms, whereby a lower impedance indicates a higher quality of the connection at the patient/electrode interface. In one embodiment, there may be a scale of connection quality data identifiers that, based on the resulting impedance, provide a user with a greater level of information about the connection quality beyond "good" and "poor". While measurement of connection quality data is described for the first electrode as the selected electrode, one skilled in the art will appreciate that these configurations may be employed for any three electrodes connected to the patient in a like manner.

The monitoring device 11 further includes an alarm 26, a communication processor 28 and a display 30 each connected to the control processor 18. Upon determining connection quality data of a selected electrode 14a, the control processor 18 may provide the connection quality data for output to a user. In one embodiment, should the connection quality data determined for the selected electrode indicate the connection is poor, the control processor 18 may automatically cause an alarm 26 to be issued. The alarm may be any of a tactile, audio or visual alarm (or any combination thereof) that notifies a healthcare practitioner that the connection of at least one electrode is poor thereby enabling the healthcare practitioner to rectify the connection to the patient to ensure high quality patient monitoring. In another embodiment, the connection quality data for each electrode can be collected and provided to a communication processor 28 for communicating the connection quality data to a remote system. The communication processor 28 may be connected to a communication network (wired or wireless) and transmit connection quality data to a patient management system for inclusion in a patient record. The communication processor 28 may employ known communication protocols to communicate over cellular networks, local area network and/or wide area networks. In a further embodiment, connection quality data may be used to modify a display image on a display device. For example, the control processor 18 may generate a connection quality indicator to be associated with each electrode and display the connection quality indicator on the display 30. In the event that the connection quality is good, the connection quality indicator may be displayed in a first format or style. If the connection quality is ever determined to be poor, the control processor 18 may cause the connection quality indicator to change to a different format or style that notifies a user that the connection quality is poor. The manner in which the connection quality data may be used is described for purposes of example only and the connection quality data may be used for any purpose to provide patient care.

In another embodiment, the patient monitoring device may be an Electroencephalograph monitor (EEG) that senses the electrical activity along the scalp to measure voltage fluctuations resulting from ionic current flows within the neurons of the brain. In this embodiment, the principles described above may be applied in a similar manner whereby the connection quality of individual electrodes connected to the patient's scalp may be determined. However, the current applied to the electrode being measured in the case of an EEG may be an AC current as opposed to a DC current.

Figure 2:
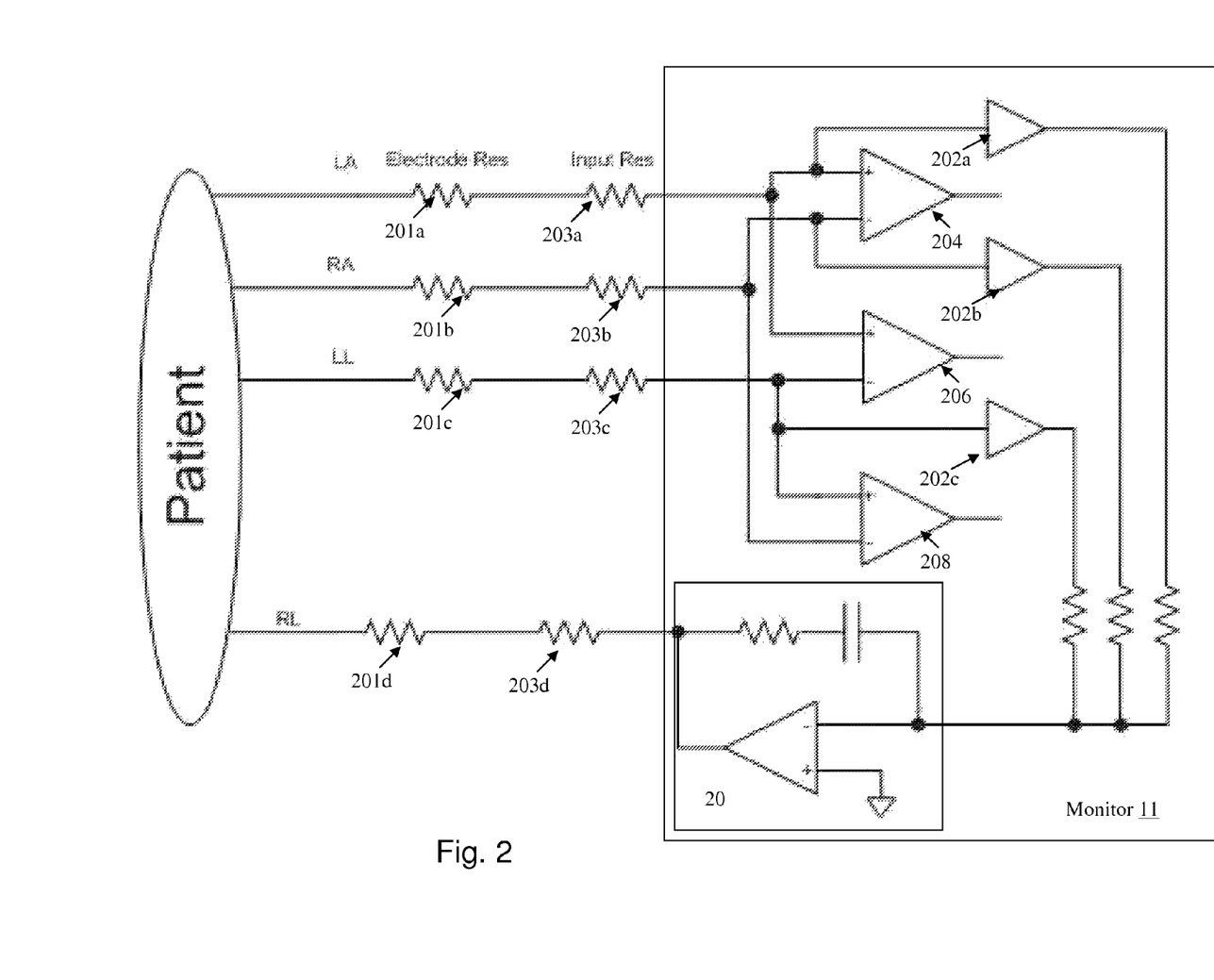
FIG. 2 depicts an exemplary circuit diagram of an ECG monitor connected to a patient according to invention principles.

FIG. 2 is a circuit diagram showing the monitoring device 11 of FIG. 1 and the connection of the primary electrodes and drive electrodes to a patient. As shown herein the monitoring device is an ECG monitor and the electrodes LA, RA and LL are the primary electrodes and RL is a the drive electrode. The RL electrode is coupled to the drive signal generator 20 that provides the patient drive signal via the RL electrode. Each of electrodes LA, RA and LL are connected to the drive signal generator 20 via respective unity gain buffer amplifiers 202a-202c. The unity gain amplifiers 202a-202c receive the voltages sensed by the monitoring device 11 which may be used individually or collectively as the sensed voltages that regulate the drive signal generator 20 over electrode RL.

A series of amplifiers 204, 206 and 208 are provided and are used to measure the voltage differences between respective primary leads comprised of electrodes LA, RA and LL. Each amplifier 204, 206 and 208 includes a positive input and a negative input to which the electrodes are connected. The polarity of these inputs is relevant to the monitoring of electrical impulse data, the purpose and configuration of which are known to one skilled in the art. The LA electrode is coupled to a positive input of a first amplifier 204 and a positive input of the second amplifier 206. The RA electrode is coupled to a negative input of the first amplifier 204 and a negative input of the third amplifier 208. The LL electrode is coupled to a negative input of the second amplifier 206 and a positive input of the third amplifier 208. Additionally, each of the electrodes LA, RA, LL and RL include an electrode resistance 201a-201d and an input resistance 203a-203d. The electrode resistance 201a-201d represents the resistance associated with securing the electrode to the patient and the input resistance 203a-203d is a fixed resistance (~20-50KΩ) which provides protection for the monitoring device during defibrillation. This configuration advantageously enables determination of the voltage differences between each of the electrodes in the manner discussed below.

Figure 3:
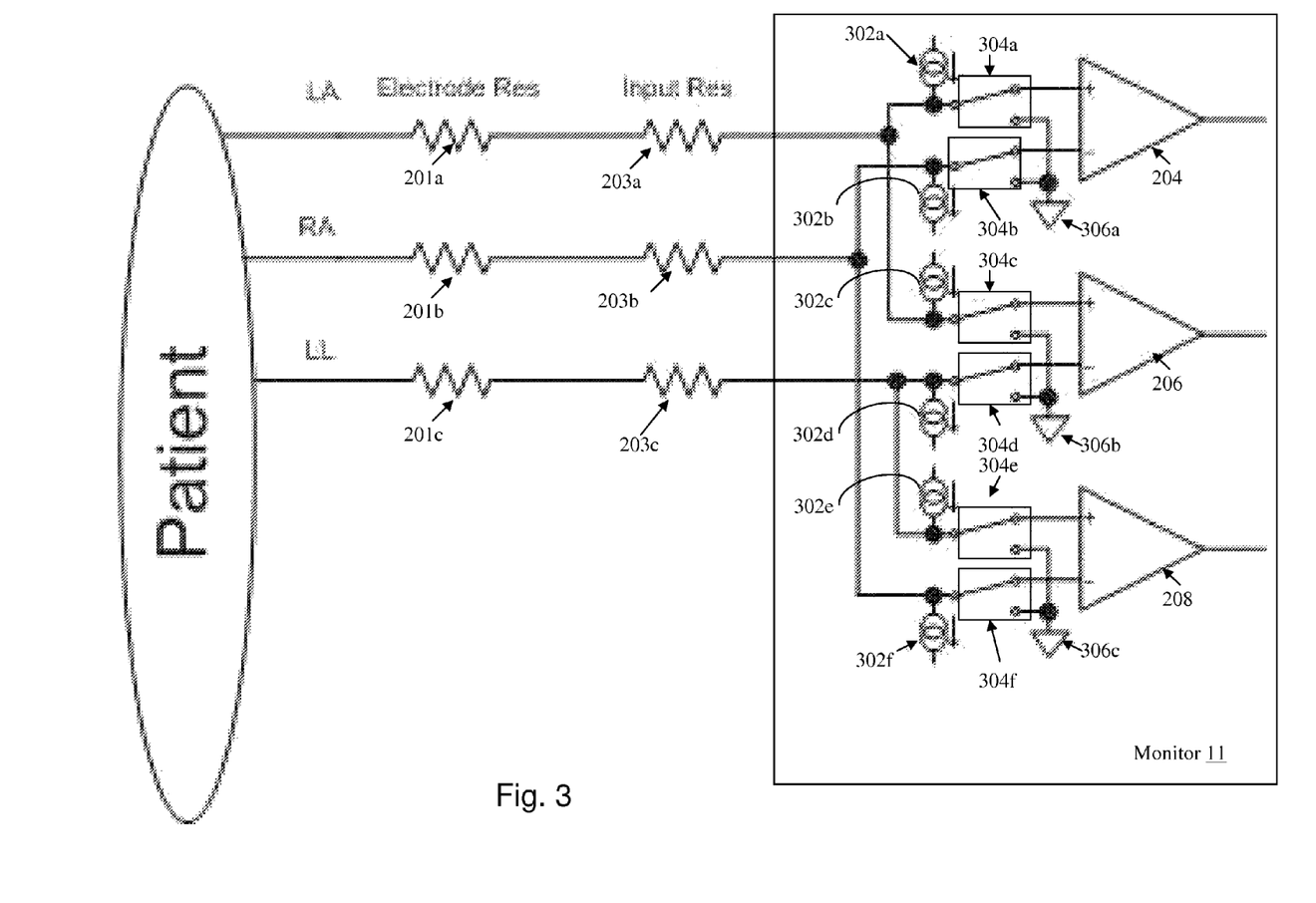
FIG. 3 is an exemplary circuit diagram of the patient electrode impedance measurement apparatus according to invention principles.

FIG. 3 is a circuit diagram showing the connection of electrodes LA, RA, LL to the amplifiers 204, 206 and 208 (e.g. instrumentation amplifiers) to show how the apparatus calculates electrode connection quality data. The LA electrode is connected to the positive input of the first amplifier 204 via a first switch 304a. The first switch 304a is movable between a first position connecting the LA electrode to the positive input of the first amplifier 204 and a second position connecting the LA electrode to ground 306a. The LA electrode is also connected to the positive input of the second amplifier 206 by a third switch 304c. The third switch 304c is movable between a first position connecting the LA electrode to the positive input of the second amplifier 206 and a second position connecting the LA electrode to ground 306b.

The RA electrode is connected to the negative input of the first amplifier 204 via a second switch 304b. The second switch 304b is movable between a first position connecting the RA electrode to the negative input of the first amplifier 204 and a second position connecting the RA electrode to ground 306a. The RA electrode is also connected to the negative input of the third amplifier 208 by a sixth switch 304f. The sixth switch 304f is movable between a first position connecting the RA electrode to the negative input of the third amplifier 208 and a second position connecting the RA electrode to ground 306b.

The LL electrode is connected to the negative input of the second amplifier 206 via a fourth switch 304d. The fourth switch 304d is movable between a first position connecting the LL electrode to the negative input of the second amplifier 206 and a second position connecting the LL electrode to ground 306b. The LL electrode is also connected to the positive input of the third amplifier 208 by a fifth switch 304e. The fifth switch 304e is movable between a first position connecting the LL electrode to the positive input of the third amplifier 208 and a second position connecting the LL electrode to ground 306c.

A current source 302a-302f is coupled to the wire connecting the electrode to the patient. The current source applies a fixed current (~10 nanoamps) to a respective one of the electrodes for which a connection quality measurement is desired. As shown herein, each of the switches 304a-f are shown connecting their respective electrodes to their respective inputs on amplifiers 204, 206 and 208. This configuration indicates that the ECG monitoring device is monitoring the electrical signals of the patient to generate an ECG waveform in a known manner. Alternatively, a single current source may be connected to each of the electrodes through a multiplexer/switch which selectively (or sequentially) applies the current to one of the electrodes.

Figure 4:
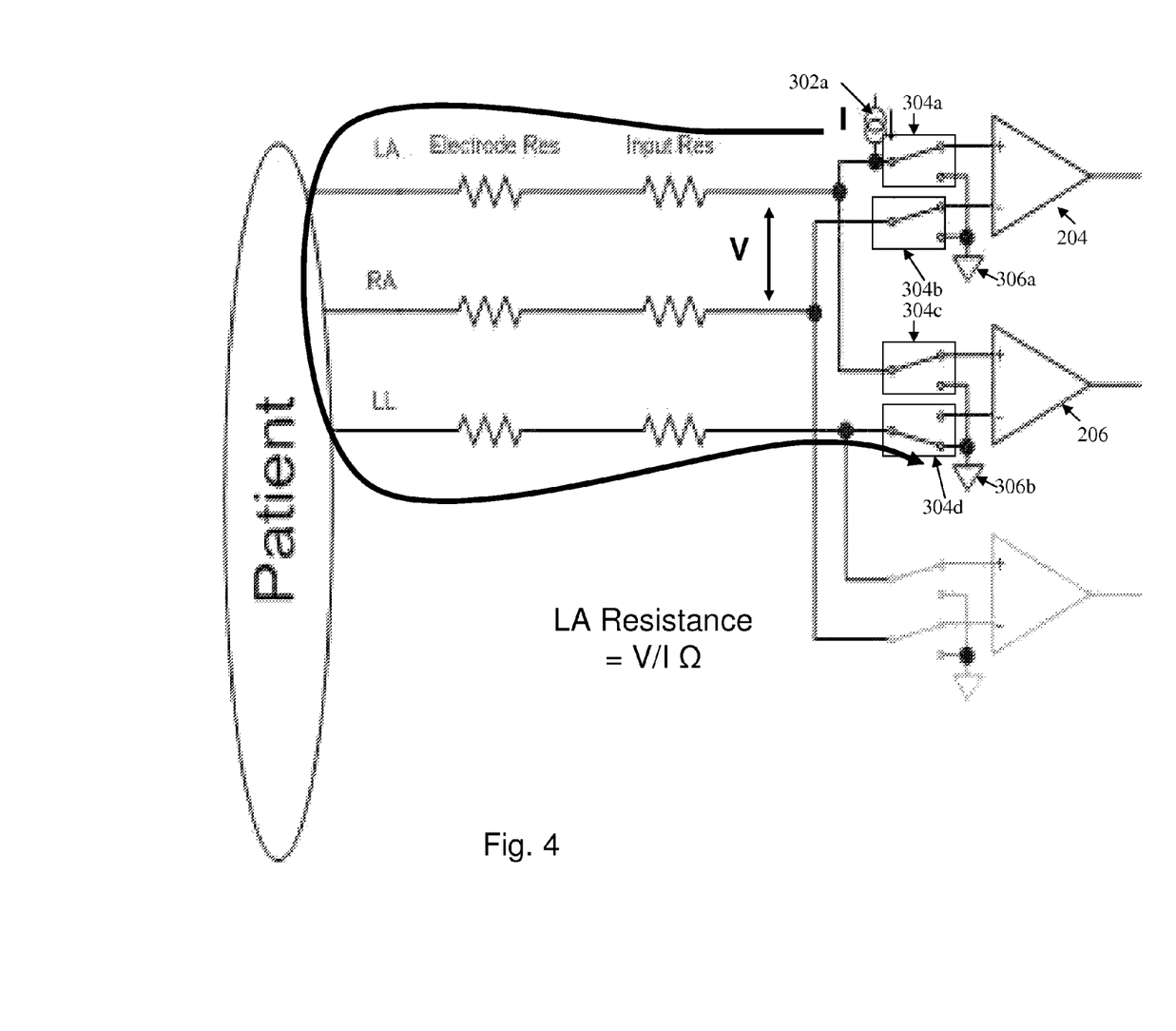
FIG. 4 is an exemplary circuit diagram of the patient electrode impedance measurement apparatus according to invention principles.

FIG. 4 is a circuit diagram showing the configuration of the switches described in FIG. 3 when connection quality data is sought for electrode LA. When the control processor 18 (FIG. 1) identifies and selects an electrode to determine the connection quality thereof, the control processor 18 disables the drive signal generator 22 (FIG. 2). Although not shown herein, upon disabling the drive signal generator electrode RL becomes a conventional input lead, the impedance of which may be measured as discussed below. The first switch 304a and the third switch 304c are caused to connect the LA electrode with the positive inputs of the first and second amplifiers 204 and 206, respectively. The second switch 304b is caused to connect the RA electrode to the negative input of the first amplifier 204 and the fourth switch 304d is caused to connect the LL electrode to ground 306b. The control processor 18 causes the current source 302a to apply a current (I) to the LA electrode. Current (I) flows in the direction indicated by the arrow labeled with reference numeral 402. Current (I) flows through the LA electrode, through the patient and back to ground via the LL electrode. As current flows, voltage at the LA electrode and the RA electrode are input to the first amplifier 204 which calculates the voltage difference between the LA electrode and the RA electrode represented in FIG. 4 as (V). The control processor calculates the impedance at the LA electrode by dividing the voltage difference between LA and RA electrodes by the current (I).

While the measurement of the LA electrode is described herein, one skilled in the art will appreciate how the respective switches may be configured to derive connection quality data for each lead. For example, to determine connection quality data for the RA electrode, the switch configuration would be the same as discussed above with the exception that the current source 302b as shown in FIG. 2 would be used to apply the current to the RA electrode. The current flows through the RA electrode, through the patient and back to ground via the LL electrode. The voltage difference (V) would be calculated between the RA electrode and the LA electrode and the impedance of RA is calculated by dividing the voltage difference between RA and LA by the current applied to the RA electrode. Other similar switch configurations are readily discernable by a person skilled in the art.

The calculated impedance at the LA electrode may be transformed into connection quality data by comparing the calculated impedance with a threshold impedance value whereby a lower calculated impedance corresponds to a higher quality connection between the electrode and the patient. The connection quality data advantageously provides a user with information regarding non-driven leads allowing the user to identify which non-driven leads could be used as driven leads if needed. Additionally, the connection quality data further advantageously provides the healthcare practitioner with information that allows the practitioner (or control processor 18) to select which electrode combinations should be used to provide ECG lead data.

Figure 5:
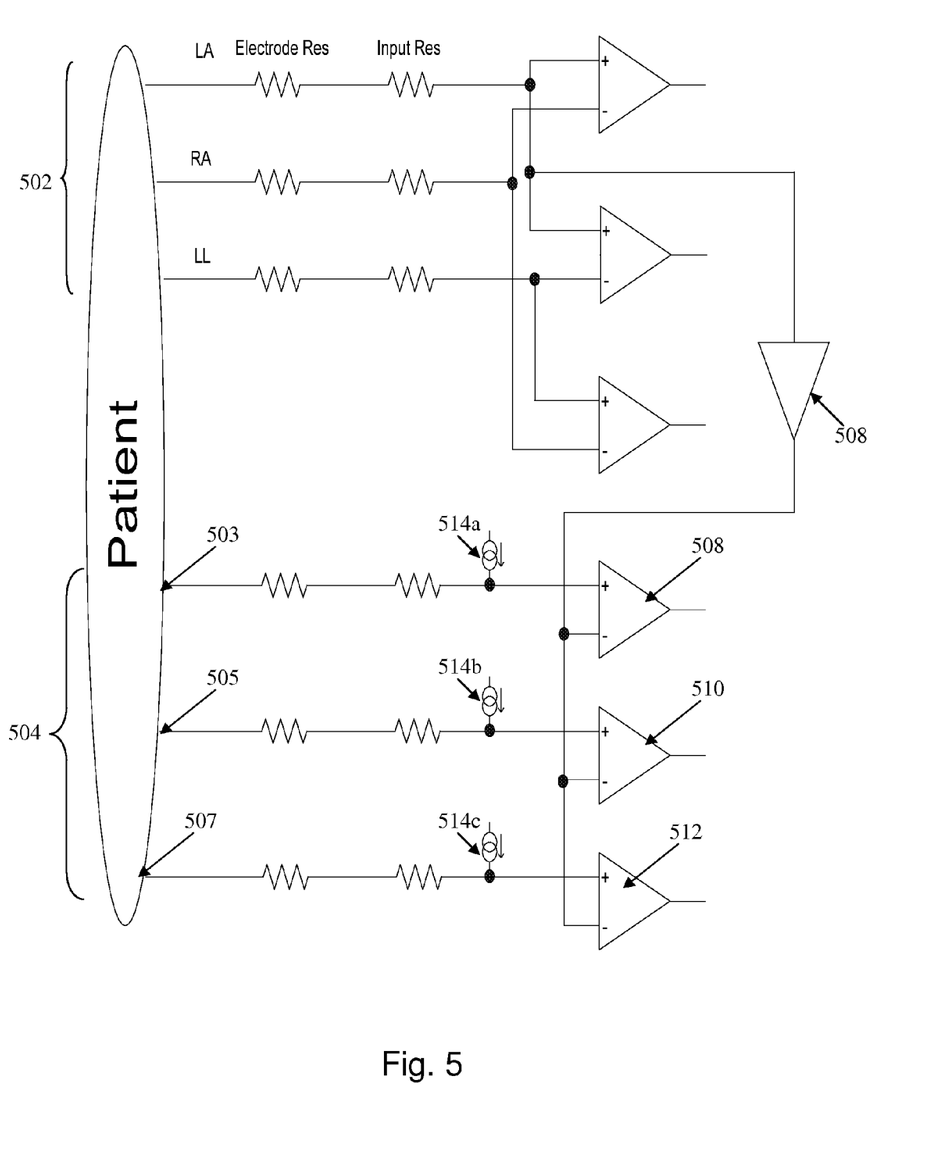
FIG. 5 is an exemplary circuit diagram of the patient electrode impedance measurement apparatus according to invention principles.

FIG. 5 is a circuit diagram of another embodiment of the apparatus according to invention principles. FIG. 5 shows, in addition to the primary electrodes discussed above in FIGS. 2-4, a set of non-primary electrodes 504. In the case of an ECG monitoring setup, the non-primary electrodes may include at least one of the driven lead (RL) and any combination of the chest electrodes V1-V6. In this embodiment, the set of non-primary electrodes includes electrodes 503, 505 and 507. Additionally, for purposes of simplicity the switches connect the electrodes 503, 505 and 507 to either respective inputs of an amplifier or a ground are not shown. However, these switches are present and connect the respective non-primary electrodes to amplifiers 508, 510, and 512 in a like manner. Additionally, a unity gain buffer 506 conveys the reference voltage derived from the primary electrodes to the negative input of each amplifier 508, 510 and 512. This reference voltage serves as a point of comparison between a voltage on a selected non-primary lead to which current is applied.

In operation, to measure the impedance at electrode 503, current (I) from current source 504a is applied to the electrode and at least one of the switches connecting electrodes 505 and 507 to amplifiers 510 and 512, respectively, are switched to ground. The current flows from current source 504a through the electrode 503, through the patient and back to ground via one or both electrodes 505 and 507 depending on which one (or both) is coupled to ground. A difference between a voltage generated at electrode 503 and the reference voltage is calculated by the unity gain buffer 506. The resulting voltage difference is divided by the current applied to the electrode 503 to determine an impedance of electrode 503. Connection quality data is calculated in a manner similar to that discussed above.

While only three additional non-primary electrodes 503, 505 and 507 are shown, one skilled in the art understands that any number of additional electrodes used to monitor electrical impulses of the patient may be used and connection quality data for each electrode may be calculated as discussed above.

Figure 6:
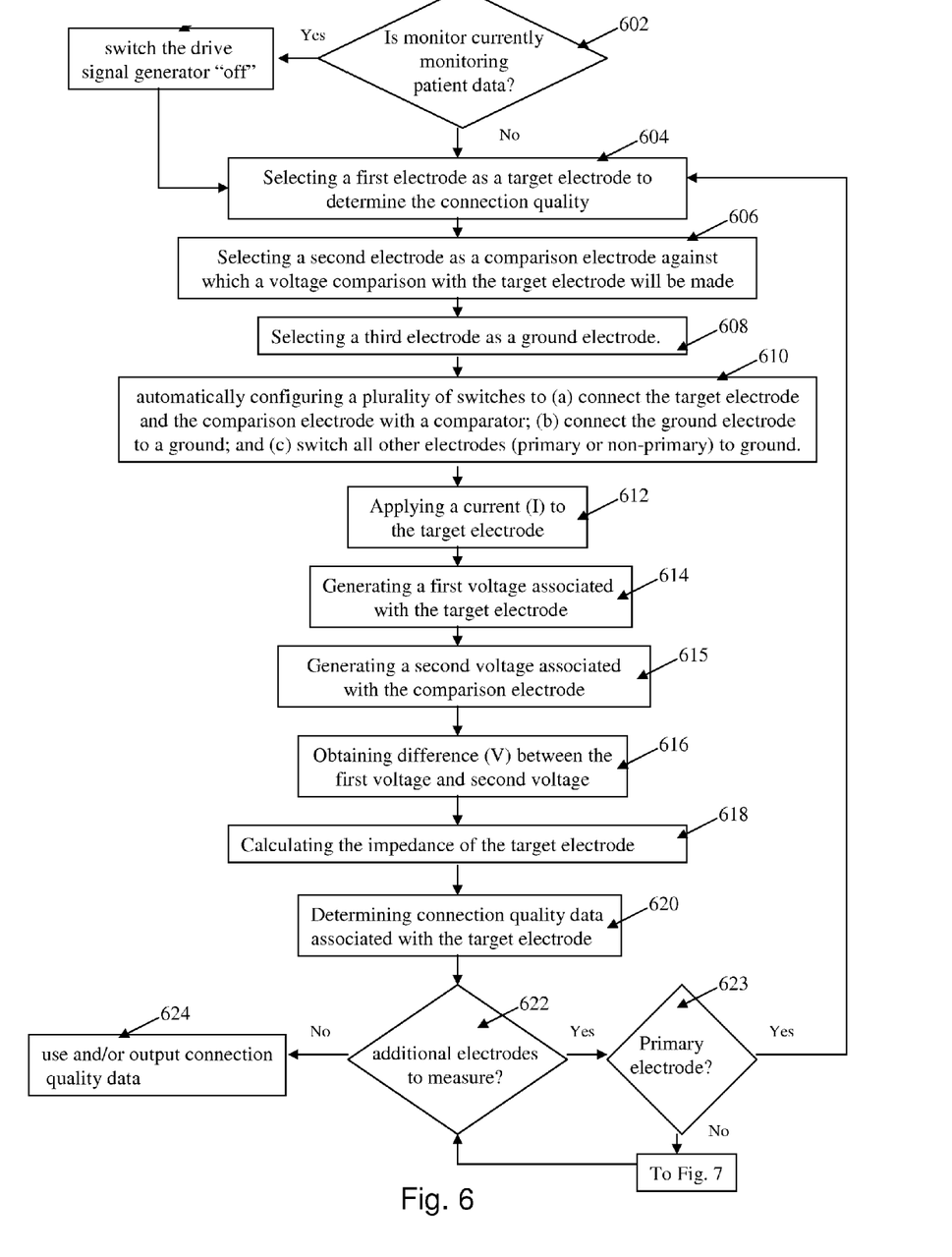
FIG. 6 is a flow diagram detailing the operation of the patient electrode impedance measurement apparatus according to invention principles.

FIG. 6 is a flow diagram detailing how the apparatus calculates connection quality data for each electrode. At step 602, the control processor determines if the monitoring device is currently monitoring patient data via electrodes connected to the patient. If the monitor is monitoring patient data, the control processor, at step 603, switches the drive signal generator "off" resulting in the drive lead acting as another input through which patient data could be monitored and system operation continues at step 604. If the monitoring device is not currently monitoring patient data via the electrodes, system operation continues at step 604.

At step 604, a target electrode is selected by the control processor to determine the connection quality at the patient/electrode interface. At step 606, a second electrode is selected as a comparison electrode against which a voltage comparison with the target electrode will be made. At step 608, an electrode is selected as a ground electrode. At step 610, the control processor automatically configures a plurality of switches to (a) connect the target electrode and the comparison electrode with an instrumentation amplifier; (b) connect the ground electrode to a ground; and (c) switch all other electrodes (primary or non-primary) to ground. At step 612, a current (I) is applied to the target electrode such that the current flows through the target electrode, through the patient and to ground via the ground electrode. As the current flows, a first voltage associated with the target electrode is generated in step 614 and a second voltage associated with the comparison electrode is generated in step 615. Steps 614 and 615 may occur simultaneously or sequentially. A difference (V) between the first voltage and second voltage is computed in step 616 by the amplifier and the impedance of the target electrode is calculated in step 618 by dividing voltage difference (V) by the current (I) applied to the target electrode. The connection quality data associated with the target electrode is determined in step 620 by comparing the result of the calculation in step 618 with a threshold impedance and determining if the impedance of the target electrode is greater than or equal to a threshold impedance. In step 622, the control processor queries whether there additional electrodes for which a connection quality measurement is needed. If so, a determination as to the type of electrode to be measured is made in step 623. If the additional electrode is a primary electrode, then system operation returns to step 604. If the additional electrode(s) are non-primary electrodes, system operation continues in FIG. 7. If the determination in step 622 is negative, the system may use and/or output connection quality data in step 624 to at least one of (a) notify a practitioner regarding the connection quality of one or more leads; (b) return to monitoring the patient; and (c) automatically adjust patient monitoring settings to obtain patient parameter data from an electrode or set of electrodes having the highest quality connection as determined as a function of impedance of the electrodes.

Figure 7:
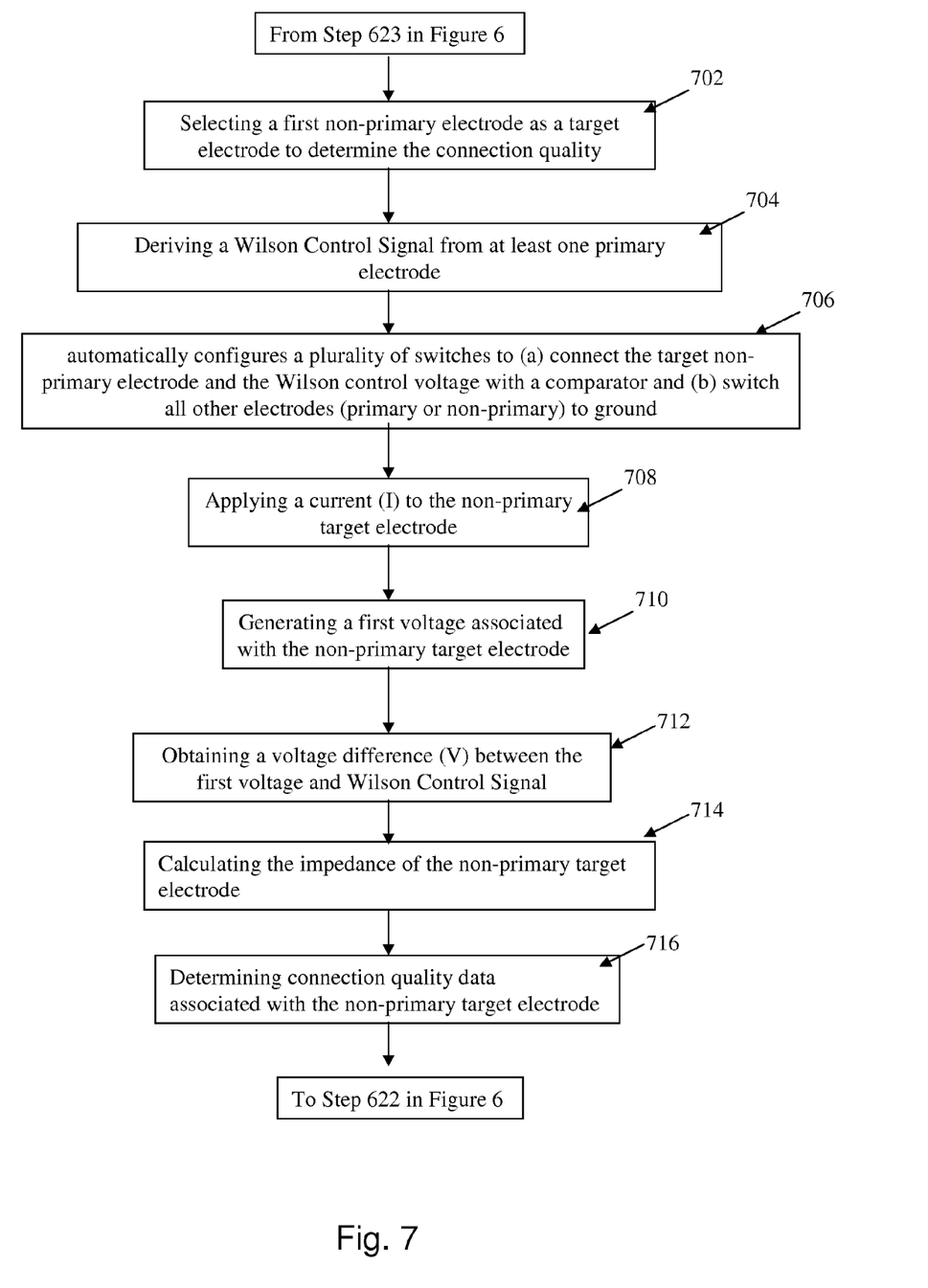
FIG. 7 is a flow diagram detailing the operation of the patient electrode impedance measurement apparatus according to invention principles

FIG. 7 is a flow diagram detailing how connection quality data is derived for non-primary electrodes. FIG. 7 begins at step 623 in FIG. 6. The control processor selects a non-primary electrode as the target non-primary electrode in step 702. A reference voltage is derived by a unity gain amplifier from at least one primary electrode in step 704 for use as a point of comparison with the target non-primary electrode. In step 706, the control processor automatically configures a plurality of switches to (a) connect the target non-primary electrode and the reference voltage with an instrumentation amplifier and (b) switch all other electrodes (primary or non-primary) to ground. At step 708, a current (I) is applied to the non-primary target electrode such that the current flows through the non-primary target electrode, through the patient and to ground via the ground electrode. As the current flows, a first voltage associated with the non-primary target electrode is generated in step 710. A voltage difference (V) between the first voltage and reference voltage from the unity gain amplifier is computed in step 712 and the impedance of the non-primary target electrode is calculated in step 714 by dividing the voltage difference (V) by the current (I) applied to the target electrode. The connection quality data associated with the target electrode is determined in step 716 by comparing the result of the calculation in step 714 with a threshold impedance and determining if the impedance of the target electrode is greater than or equal to a threshold impedance. System operation reverts back to step 622 in FIG. 6.

It is important to note that the connection quality data measurement may be calculated at predetermined intervals during the course of a patient being monitored. At the time the connection quality data is being measured, the patient drive signal is disconnected in order to determine the connection quality of the electrode. Determining connection quality data for a single electrode takes less than one millisecond and thus measuring connection quality for each electrode can occur during the time between ECG waveforms. In this embodiment, the drive signal generator is disconnected and the apparatus pauses to settle for substantially a microsecond prior to configuring the switches to connect the electrodes in the desired manner to measure connection quality data for the respective electrode. As connection quality data may only be measured for a single electrode between successive ECG waveforms, the control processor may execute a routine to sequentially measure all electrodes between ECG waveforms. In this embodiment, the control processor may keep track of the electrodes that have been measured until connection quality data for all electrodes has been determined. In another embodiment, the control processor may selectively measure a set of electrodes from the plurality of electrodes connected to the patient during the waveform re-trace period. In this embodiment, the control processor may keep track of the sets of electrodes for which connection quality data has been determined until connection quality data for all electrodes has been determined that have been measured The intervals during which the connection quality data are measured may be pre-stored in the control processor or selectively configurable by a user.

The apparatus described above with respect to FIGS. 1-7 may advantageously determine the connection quality for each electrode connected to a patient. This advantageously provides a user with information regarding the connection at each electrode and allows a user to improve monitoring configurations to take into account and utilize electrodes to derive leads that have a higher quality connection. This further enables a user to remedy a degraded connection to improve the quality of the patient data being monitored.

Although the invention has been described in terms of exemplary embodiments, it is not limited thereto. Rather, the appended claims should be construed broadly to include other variants and embodiments of the invention which may be made by those skilled in the art without departing from the scope and range of equivalents of the invention. This disclosure is intended to cover any adaptations or variations of the embodiments discussed herein.

What is claimed is:

1. An apparatus that determines a connection quality of an electrode to a patient, the apparatus comprising:
   a current source connected to a first electrode;
   a switch connected to a second electrode for selectively connecting the second electrode to ground; and
   a processor connected to the first electrode and a third electrode, said processor detecting a voltage difference between the first electrode and the third electrode upon application of a current to the first electrode by said current source to determine connection quality data for the first electrode,
   wherein said apparatus is connected to electrodes of an ECG monitor and said processor disables a drive electrode of the ECG monitor prior to measuring connection quality data.

2. The apparatus as recited in claim 1, wherein said processor includes an instrumentation amplifier that compares the voltage of the first and the third electrodes to determine the voltage difference; and
   a control processor that calculates an impedance of the first electrode from the voltage difference and current applied by said current source.

3. The apparatus as recited in claim 2, wherein said processor is connected to a plurality of electrodes and further comprising a plurality of switches, each of said plurality of switches being movable between a first position connecting a respective electrode of said plurality of electrodes to the processor and a second position connecting the respective electrode to ground.

4. The apparatus as recited in claim 3, wherein the current source applies current to one of the plurality of electrodes to measure a connection quality of the one of said plurality of electrodes.

5. The apparatus as recited in claim 4, wherein the one of said plurality of electrodes is connected by its respective switch to said processor.

6. The apparatus as recited in claim 4, wherein at least one other electrode of said plurality of electrodes is connected to ground by its respective switch.

7. The apparatus as recited in claim 3, wherein the plurality of electrodes includes a set of primary electrodes and set of secondary electrodes and said processor calculates connection quality data of a respective one of the secondary electrodes by detecting a voltage difference between the respective one of the secondary electrodes and a reference voltage upon application of a current to the respective one of the secondary electrodes by said current generator.

8. The apparatus as recited in claim 7, wherein at least one other of the secondary electrodes are connected to ground by its respective switch.

9. The apparatus as recited in claim 1, wherein said connection quality data is determined by dividing the voltage difference between the first and third electrodes by the current applied to the first electrode to determine an impedance of the first electrode; and
   comparing the impedance with a threshold impedance level.

10. The apparatus as recited in claim 9, wherein connection quality data indicates a good connection when the impedance is less than a threshold value and indicates a poor connection when the impedance is greater than the threshold value.

11. The apparatus as recited in claim 1, further comprising at least one of (a) an alarm that notifies a user of a poor in response to said connection quality data; (b) a display that displays an indicator representative of said connection quality data to a user; or (c) a communication processor that selectively communicate said connection quality data to a remote computing system via a communication network.

12. An ECG monitoring apparatus that that determines a connection quality of an electrode connected to a patient, the apparatus comprising:
   a plurality of electrodes coupled to a patient, each of said plurality of electrodes sensing electrical impulses representing at least one patient parameter from the patient;
   a current source selectively connectable to the plurality of electrodes that selectively applies a current to any of the plurality of electrodes;
   a processor that receives electrical impulses from the patient via the plurality of electrodes and calculates connection quality data for respective ones of the plurality of electrodes;
   a plurality of switches, each switch connected to a respective one of said plurality of electrodes and said processor and movable between a first position connecting a respective electrode to said processor and a second position connecting said respective electrode to ground; wherein a first switch connects an electrode being monitored to said processor, and a second switch connects a second electrode to said processor; and at least one other of said plurality of switches connects respective ones of said plurality of electrodes to ground, and said processor detects a voltage difference between said first electrode and said second electrode upon application of a current to said first electrode by said current source to determine connection quality data for said first electrode which is based on an impedance measurement between one of the plurality of electrodes and the patient; and
   a drive electrode that is disabled by the processor prior to calculating connection quality data.

13. A method of determining a connection quality of an electrode connected to a patient, the method comprising:
   connecting a first electrode of a plurality of electrodes to (i) a processor, (ii) a first non-inverting input of a first amplifier, and (iii) a second non-inverting input of a second amplifier;
   connecting a second electrode of a plurality of electrodes to (i) ground, (ii) a first inverting input of the first amplifier, and (iii) a third inverting input of a third amplifier;
   connecting a third electrode of a plurality of electrodes to (i) the processor, (ii) a second inverting input of the second amplifier, and (iii) a third non-inverting input of the third amplifier;
   applying a current from a current source to the first electrode;
   detecting a voltage difference between the first electrode and a third electrode; and
   determining connection quality data of the first electrode using the voltage difference between the first and third electrode.

14. The method as recited in claim 13, wherein the activity of determining connection quality data further comprises: comparing the voltage of the first and third electrodes to determine the voltage difference using an instrumentation amplifier; and calculating an impedance of the first electrode from the voltage difference and applied current.

15. The method as recited in claim 13, further comprising the activity of providing a plurality of electrodes selectively connected to a patient; designating a first set of said plurality of electrodes as primary electrodes; and designating a second set of said plurality of electrodes as secondary electrode.

16. The method as recited in claim 15, further comprising the activity of: determining if the first electrode is a primary electrode or a secondary electrode; and in response to determining the first electrode of the plurality of electrodes is a secondary electrode, connecting the first electrode to the processor and connecting at least one other of the plurality of electrodes to ground; applying current from a current source to the first electrode; detecting a voltage difference between the first electrode and a reference voltage; and determining connection quality data of the first electrode using the voltage difference between the first electrode and the reference voltage.

17. The method as recited in claim 13, wherein said method is performed by an ECG monitor that selectively monitors the electrical impulses of a patient via a plurality of electrodes.

* * * * *